United States Patent [19]

Paoletti

[11] Patent Number: 5,204,243
[45] Date of Patent: Apr. 20, 1993

[54] RECOMBINANT POXVIRUS INTERNAL CORES

[75] Inventor: Enzo Paoletti, Albany, N.Y.

[73] Assignee: Health Research Incorporated, Albany, N.Y.

[21] Appl. No.: 480,097

[22] Filed: Feb. 14, 1990

[51] Int. Cl.$^5$ .................. C12P 21/00; C12N 7/01; C12N 7/04; A61K 39/00

[52] U.S. Cl. .................. 435/69.1; 435/69.3; 435/91; 435/235.1; 435/236; 435/320.1; 424/89; 424/93 A

[58] Field of Search ............. 435/235.1, 69.1, 69.3, 435/172.3, 320.1, 91; 424/89, 93, 93 A; 935/32, 34, 36, 57, 65

[56] References Cited

FOREIGN PATENT DOCUMENTS 8903429 4/1989 PCT Int'l Appl. .

OTHER PUBLICATIONS

Kates, S., et al., 1970, *Chemical Abstracts*, vol. 73, p. 7, abstracts 52242-52243.
Franke, C. A., et al., 1987, *Arch. Virol.*, vol. 94, pp. 347-351.
Espositor, J. J., et al., 1989, Advances in Veterinary Science and Comparative Medicine, vol. 33, pp. 195-247.
Fenner, F., 1985, In:Virology, ed., B. N. Fields et al., (Raven Press), New York, p. 665.
Clewell, D. B., J. Bacteriol., 110, 667-676 (1972).
Clewell, D. B. and D. R. Helinski, Proc. Natl. Acad. Sci. U.S.A., 62, 1159-1166 (1969).
Easterbrook, K. B., J. Ultrastruct. Res., 14, 484-496 (1966).
Joklik, W., Virology, 18, 9-18 (1962).
Katz, E. and B. Moss, J. Virol., 6, 717-726 (1970).
Paoletti, E., H. Rosemond-Hornbeak and B. Moss, J. Biol. Chem., 249, 3273-3280 (1974).
Piccini, A., M. E. Perkus and E. Paoletti, In: Methods in Enzymology, vol. 153, eds. Wu, R., and L. Grossman, (Academic Press), pp. 545-563 (1987).
Taylor, J., R. Weinberg, B. Languet, P. Desmettre and E. Paoletti, Vaccine, 6, 497-503 (1988).
Taylor, J., R. Weinberg, Y. Kawaoda, R. G. Webster and E. Paoletti, Vaccine, 6, 504-508 (1988).
Dales, S. and B. G. T. Pogo, In: Biology of Poxviruses, eds., Kingsbury, D. W. and H. Zur Hausen, (Springer-Verlag, New York), (1981), pp. 77-82.
Fenner, F., R. Wittek and K. R. Dumbell, In: The Orthopoxviruses, (Academic Press), p. 53 (1989).
Moss, B., In: Fields Virology, vol. 2, eds., Fields, B. N. and D. M. Knipe, (Raven Press, New York), pp. 2079-2111 (1990).
Biology Today, Second Edition, 1975, pp. 46-48, Kirk et al., CRM/Random House, New York.
Biological Science, Third Edition, 1980, pp. 77-78 and 920-921; Keetor, W. J.; Norton, New York.
Intergrated Principles of Zoology, Fifth Edition, 1974, p. 5; Hickman, C. P. et al.; C. V. Mosby Company, St. Louis.

*Primary Examiner*—Richard A. Schwartz
*Assistant Examiner*—Mary E. Mosher
*Attorney, Agent, or Firm*—Curtis, Morris & Safford

[57] ABSTRACT

What is described is a modified recombinant poxvirus, such as vaccinia virus, fowlpox virus and canarypox virus, having an internal core containing DNA from a non-pox source in a nonessential region of the poxvirus genome. The recombinant poxvirus is modified by disassociating the internal core from outer membranes of the poxvirus. The DNA codes for and expresses a gene product in a cell cultured in vitro and in a host in vivo without productive replication of the virus in the cell or in the host. What is also described is a vaccine containing the modified recombinant poxvirus for inducing an immunological response in a host inoculated with the vaccine.

17 Claims, No Drawings

RECOMBINANT POXVIRUS INTERNAL CORES

FIELD OF THE INVENTION

The present invention relates to a modified recombinant poxvirus and to methods of making and using the same. More in particular, the invention relates to recombinant poxvirus modified by disassociating the internal core from the outer membranes of the poxvirus, which modified recombinant poxvirus expresses gene products in a host without productive replication of the poxvirus in the host, and to vaccines containing the modified recombinant poxvirus.

Several publications are referenced in this application by arabic numerals within parentheses. Full citation to these references is found at the end of the specification immediately preceding the claims. These references describe the state-of-the-art to which this invention pertains.

BACKGROUND OF THE INVENTION

The family Poxviridae is subdivided into two subfamilies. Chordopoxvirinae infect vertebrates whereas the subfamily Entomopoxvirinae infect insects. At least six genera comprise the subfamily Chordopoxvirinae. Virions of all genera of chordopoxviruses are similar except those in the genus Parapoxvirus. The virions are complex i.e. they do not conform to the two types of symmetry found in most other viruses. There is a dumbbell shaped core wherein is contained the double stranded DNA genome of the virus. Associated with the core are a number of enzymes involved in transcription. There are two lateral bodies of unknown function that reside within the concavities of the dumbbell shaped core. These structures are enclosed by a membrane like structure. In addition, an envelope consisting of lipids and several viral specified polypeptides can be found on the small percentage of extracellular virus.

The virion infects cells by fusion with plasma membrane of the cell or via endocytosis, the process by which cells ingest foreign objects in a non-specific fashion. Once internalized the outer membranes of the virus are released and the transcriptional machinery of the cores is activated. Thus begins the genetic expression of poxvirus functions.

Viral cores can be prepared chemically in vitro in the presence of nonionic detergents and reducing reagents (3,5,7). Differential centrifugation of the chemically disrupted virions allows the purification of cores away from disrupted membrane material.

Viral cores thus prepared are transcriptionally active and have been used as starting material for the purification of many enzymatic functions of the virion that are associated with transcription (7, 11-13). Significantly, however, viral cores are no longer infectious i.e. when contacted with susceptible cell substrates in vitro no infectious progeny virus is produced (3).

Vaccinia and other orthopoxviruses have been genetically engineered to express foreign genes of interest in vaccine production or for the production of biologically interesting molecules in vitro. Vaccinia has a broad host range for both in vitro cell substrates and in vivo susceptible hosts.

Fowlpox and other avipox viruses have been manipulated to express foreign genes. These recombinant viruses have been useful for the production of biologically active molecules in vitro, the production of species specific avian vaccines and, interestingly, for the production of vaccines useful in non-avian species. This last point is of interest because avipoxes are restricted to avian hosts for productive infections. Inability of avipoxes to productively replicate in non-avian species provides useful properties such as perceived safety in vaccination.

The basic technique of inserting foreign genes into live infectious poxvirus involves recombination between pox DNA sequences flanking a foreign genetic element in a donor plasmid and homologous sequences present in the rescuing poxvirus (8).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an $E.$ $coli$ plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a region of pox DNA containing a nonessential locus. The resulting plasmid construct is then amplified by growth within $E.$ $coli$ bacteria (1) and isolated (2,6).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Thus, methods have been developed in the prior art that permit the creation of recombinant vaccinia viruses and avipox viruses by the insertion of DNA from any source (e.g. viral, prokaryotic, eukaryotic, synthetic) into a nonessential region of the vaccinia or avipox genome, including DNA sequences coding for the antigenic determinants of a pathogenic organism. Recombinant vaccinia viruses created by these methods have been used to induce specific immunity in mammals to a variety of mammalian pathogens, all as described in U.S. Pat. No. 4,603,112, incorporated herein by reference. Recombinant avipox viruses created by these methods have been used to induce specific immunity in avian species (10) and in non-avian species (9).

Unmodified vaccinia virus has a long history of relatively safe and effective use for inoculation against smallpox. However, before the eradication of smallpox, when unmodified vaccinia was widely administered, there was a modest but real risk of complications in the form of generalized vaccinia infection, especially by those suffering from eczema or immunosuppression. Another rare but possible complication that can result from vaccinia inoculation is post vaccination encephalitis. Most of these reactions resulted from inoculating individuals with skin diseases such as eczema or with impaired immune systems, or individuals in households with others who had eczema or impaired immunological responses. Vaccinia is a live virus, and is normally harmless to a healthy individual. However, it can be transmitted between individuals for several weeks after inoculation. If an individual with an impairment of the normal immune response is infected either by inoculation or by contagious transmission from a recently inoculated individual, the consequences can be serious.

Suitably modified poxvirus mutants carrying exogenous genes which are expressed in a host as an antigenic determinant eliciting the production by the host of antibodies to a host pathogen without productive replication of the poxvirus in the host represent novel vaccines which avoid the drawbacks of conventional vaccines employing killed or attenuated live organisms. Thus, for instance, the production of vaccines from killed organisms requires the growth of large quantities of the organisms followed by a treatment which will selectively destroy their infectivity without affecting their antigenicity. On the other hand, vaccines containing attenuated live organisms always present the possibility of a reversion of the attenuated organism to a pathogenic state. In contrast, when a recombinant poxvirus suitably modified is used as a vaccine, the possibility of reversion to a pathogenic organism is avoided since the poxvirus contains only the gene coding for the antigenic determinant of the disease-producing organism and not those genetic portions of the organism responsible for the replication of the pathogen.

Thus, it can be appreciated that a method which confers on the art the advantages of live virus inoculation but which reduces or eliminates the previously discussed problems would be a highly desirable advance over the current state of technology. This is even more important today with the advent of the disease known as acquired immune deficiency syndrome (AIDS). Victims of this disease suffer from severe immunological dysfunction and could easily be harmed by an otherwise safe live virus preparation if they came in contact with such virus either directly or via contact with a person recently immunized with a vaccine comprising such a live virus.

OBJECTS OF THE INVENTION

It is therefore an object of this invention to provide modified recombinant poxviruses, which modified recombinant poxviruses express gene products without productive replication of the poxviruses, and to provide a method of making such modified recombinant poxviruses.

It is also an object of the present invention to provide a vaccine which is capable of immunizing vertebrates against a pathogenic organism, which has the advantages of a live virus vaccine, and which has few or none of the disadvantages of either a live virus vaccine or a killed virus vaccine as enumerated above.

It is a further object of this invention to provide modified recombinant poxviruses for use in such vaccines.

It is a further object of this invention to provide a method for inducing an immunological response in avian and non-avian vertebrates to an antigen by inoculating the vertebrate with a modified recombinant poxvirus which cannot productively replicate in the host with the production of infectious virus. In this case, the virus is self-limiting, reducing the possibility of spreading to non-vaccinated hosts.

It is a still further object of the invention to provide methods for expressing a gene product in a cell cultured in vitro or in a host in vivo, which method comprises introducing into the cell culture or inoculating the host with a modified recombinant poxvirus containing DNA which codes for and expresses the gene product without productive replication of the virus.

These and other objects and advantages of the present invention will become more readily apparent after consideration of the following.

STATEMENT OF THE INVENTION

In one aspect, the present invention relates to a modified recombinant poxvirus having an internal core containing therein DNA from a non-pox source in a nonessential region of the poxvirus genome, wherein the recombinant poxvirus is modified by disassociating the internal core from outer membranes of the poxvirus, and to methods for coding for and expressing gene products using such a modified recombinant poxvirus. Advantageously, the poxvirus according to the present invention is from the subfamily Chordopoxvirinae or Entomopoxvirinae.

In another aspect, the present invention relates to a vaccine for inducing an immunological response in a host inoculated with the vaccine, said vaccine including a carrier and a modified recombinant poxvirus having an internal core containing therein DNA from a non-pox source in a nonessential region of the poxvirus genome, wherein the recombinant poxvirus is modified by disassociating the internal core from outer membranes of the poxvirus. Advantageously, the poxvirus used in the vaccine according to the present invention is from the subfamily Chordopoxvirinae or Entomopoxvirinae.

The DNA from a non-pox source codes for and expresses a gene product in a cell cultured in vitro without productive replication of the virus in the cell. The DNA from a non-pox source also codes for and expresses a gene product in a host without productive replication of the virus in the host. The host can be a vertebrate, for example a mammal. The poxvirus can be a vaccinia virus or an avipox virus. The gene product can be an antigen, and the antigen can induce an immunological response in the host. The DNA from a non-pox source can be introduced into the internal core by recombination.

DETAILED DESCRIPTION OF THE INVENTION

A better understanding of the present invention and of its many advantages will be had from the following example, given by way of illustration.

EXAMPLE

Construction of Recombinant Poxvirus Internal Core

To determine whether orthopoxvirus cores prepared by chemical procedures would be useful for eliciting immune responses in vivo, a recombinant WR vaccinia virus vP390 which contains the gene encoding the rabies virus G glycoprotein was studied (9). The rabies glycoprotein is inserted into the BamF site of the virus VTK79 and its expression is regulated by the vaccinia promoter designated C10LW (the Pi promoter) (9). The virus was cultivated by standard methods and was purified using the basic sucrose gradient method (4). Cores were prepared from this purified virus by incubation of the purified virus in a solution containing 50 mM Tris-HCl (pH8.5), 10 mM dithriothreitol and 0.5% nonidet P40 at 4° C. for 1 h. The solution was gently mixed periodically (10–15 min). Cores were recovered by centrifugation in a microfuge for 10 min. (approximately 13,000 rpm). The pelleted cores were washed with 50 mM tris-HCl, pH8.5. Cores were resuspended in 50 mM Tris-HCl, pH8.5 by indirect sonication (Sonicator W-385, Heat Systems Ultrasonic, Inc.). It is clear that modifications may be effected for the preparation of cores, for example ionic conditions, pH, divalent cations, time and temperature of incubation, repeated cycles of treatment, washing conditions to remove detergent, etc. These modifications might be useful to balance the requirements for complete production of cores i.e. no detectable infectious virus remaining in the preparation, stability of core preparation in terms of transcriptional functions, and longevity of prepared cores (shelf life).

Two rabbits were inoculated with four doses of the core preparations at different sites on the shaven back of the rabbit. Doses of $10^8$, $10^7$, $10^6$ and $10^5$ core equivalent to infectious doses of virus were administered. Serum was obtained at 2, 3 and 4 weeks post vaccination and compared with preimmune serum for the presence of antibodies reactive with rabies glycoprotein in a standard ELISA assay (9). The results are shown in the following table:

| SERUM | Rabbit # | |
| --- | --- | --- |
|  | W274 | W282 |
| Preimmune | 0 | 0 |
| Week 2 | 270* | 0 |
| Week 3 | 2430 | 30 |
| Week 4 | 7290 | 90 |

*Reciprocal of serum dilution giving a positive ELISA reactivity.

The above data shows that poxvirus cores can be effectively used for vaccination purposes.

REFERENCES

1. Clewell, D. B., J. Bacteriol. 110, 667–676 (1972).
2. Clewell, D. B. and D. R. Helinski, Proc. Natl. Acad. Sci. USA 62, 1159–1166 (1969).
3. Easterbrook, K. B., J. Ultrastruct. Res. 14, 484–496 (1966).
4. Joklik, W., Virology 18, 9–18 (1962).
5. Katz, E. and B. Moss, J. Virol. 6, 717–726 (1970).
6. Maniatis, T., E. F. Fritsch and J. Sambrook, Molecular Cloning: A Laboratory Manual, (Cold Spring Harbor Laboratory, New York) (1982).
7. Paoletti, E., H. Rosemond-Hornbeak and B. Moss, J. Biol. Chem. 249, 3273–3280 (1974).
8. Piccini, A., M. E. Perkus and E. Paoletti, In: Methods in Enzymology, Vol. 153, eds. Wu, R., and L. Grossman (Academic Press) pp. 545–563 (1987).
9. Taylor, J., R. Weinberg, B. Languet, P. Desmettre and E. Paoletti, Vaccine 6, 497–503 (1988).
10. Taylor, J., R. Weinberg, Y. Kawaoda, R. G. Webster and E. Paoletti, Vaccine 6, 504–508 (1988).
11. Dales, S. and B. G. T. Pogo, In: Biology of Poxviruses, eds. Kingsbury, D. W. and H. Zur Hausen (Springer-Verlag, New York) (1981).
12. Fenner, F., R. Wittek and K. R. Dumbell, In: The Orthopoxviruses (Academic Press) p. 53 (1989).
13. Moss, B., In: Fields Virology, Vol. 2, eds. Fields, B. N. and D. M. Knipe (Raven Press, New York) pp. 2079–2111 (1990).

What is claimed is:

1. A substantially purified recombinant poxvirus core devoid of viral envelope by in vitro modification, said core containing therein exogenous DNA in a nonessential region of the poxvirus genome; the core being capable of expression of the exogenous DNA when inoculated into a host, without production of infectious progeny.

2. A substantially purified recombinant poxvirus core as in claim 1 wherein said host is a cell cultured in vitro.

3. A substantially purified recombinant poxvirus core as in claim 1 wherein said host is a vertebrate.

4. A substantially purified recombinant poxvirus core as in claim 1 wherein said host is a mammal.

5. A substantially purified recombinant poxvirus core as in claim 1 wherein said poxvirus is a vaccinia virus.

6. A substantially purified recombinant poxvirus core as in claim 1 wherein said poxvirus is an avipox virus.

7. A substantially purified recombinant poxvirus core as in claim 1 wherein the exogenous DNA codes for and the expression thereof is an antigen.

8. A substantially purified recombinant poxvirus core as in claim 2 wherein the antigen induces an immunological response in the host.

9. A substantially purified recombinant poxvirus core as in claim 1 wherein said exogenous DNA is introduced into the said core by recombination.

10. An immunogenic composition for inducing an immunological response in a host inoculated with said composition, said composition comprising a carrier and a substantially purified recombinant poxvirus core devoid of viral envelope by in vitro modification, said core containing therein exogenous DNA in a nonessential region of the poxvirus genome; the core being capable of expression of the exogenous DNA when inoculated into the host, without production of infectious progeny.

11. The immunogenic composition of claim 10 wherein the host is a vertebrate.

12. The immunogenic composition of claim 11 wherein the host is a mammal.

13. The immunogenic composition of claim 10 wherein the poxvirus is a vaccinia virus.

14. The immunogenic composition of claim 10 wherein the poxvirus is an avipox virus.

15. The immunogenic composition of claim 10 wherein the exogenous DNA codes for and the expression thereof is an antigen.

16. A method for expressing a gene product in a cell cultured in vitro, which method comprises introducing into the cell a substantially purified recombinant poxvirus core devoid of viral envelope by in vitro modification, said core containing therein exogenous DNA in a nonessential region of the poxvirus genome; the core being capable of expression of the exogenous DNA when introduced into the cell, without production of infectious progeny.

17. A method for expressing a gene product in a host, which method comprises inoculating the host with a substantially purified recombinant poxvirus core devoid of viral envelope by in vitro modification, said core containing therein exogenous DNA in a nonessential region of the poxvirus genome; the core being capable of expression of the exogenous DNA when inoculated into the host, without production of infectious progeny.

* * * * *

UNITED STATES PATENT AND TRADEMARK OFFICE
CERTIFICATE OF CORRECTION

PATENT NO. : 5,204,243
DATED : April 20, 1993
INVENTOR(S) : Enzo Paoletti

It is certified that error appears in the above-identified patent and that said Letters Patent is hereby corrected as shown below:

Col. 6, line 55, replace "claim 1" with "claim 3"; and
      line 64, replace "claim 2" with "claim 7".

Signed and Sealed this

Thirty-first Day of January, 1995

Attest:

BRUCE LEHMAN

*Attesting Officer*     *Commissioner of Patents and Trademarks*